(12) United States Patent
Anderson et al.

(10) Patent No.: US 8,463,373 B2
(45) Date of Patent: Jun. 11, 2013

(54) TRANSDERMAL SYSTEMS FOR THE DELIVERY OF THERAPEUTIC AGENTS INCLUDING GRANISETRON USING IONTOPHORESIS

(75) Inventors: Carter R. Anderson, Inver Grove Heights, MN (US); Walter L. Sembrowich, North Oaks, MN (US); Russell L. Morris, Lindstrom, MN (US); Robert Cohen, Eden Prairie, MN (US)

(73) Assignee: Teikoku Pharma USA, Inc., San Jose, CA (US)

( * ) Notice: Subject to any disclaimer, the term of this patent is extended or adjusted under 35 U.S.C. 154(b) by 12 days.

(21) Appl. No.: 12/955,043

(22) Filed: Nov. 29, 2010

(65) Prior Publication Data
US 2011/0087154 A1    Apr. 14, 2011

Related U.S. Application Data

(63) Continuation of application No. 11/112,196, filed on Apr. 22, 2005, now Pat. No. 7,856,263.

(51) Int. Cl.
*A61N 1/30* (2006.01)
*A61M 31/00* (2006.01)

(52) U.S. Cl.
USPC ............... 604/20; 604/500; 604/67; 600/573

(58) Field of Classification Search
USPC .................. 604/20, 501, 67; 600/573
See application file for complete search history.

(56) References Cited

U.S. PATENT DOCUMENTS

| | | | |
|---|---|---|---|
| 4,708,716 A * | 11/1987 | Sibalis | 604/20 |
| 4,927,408 A | 5/1990 | Haak et al. | |
| 5,207,752 A | 5/1993 | Sorenson et al. | |
| 5,224,927 A * | 7/1993 | Tapper | 604/20 |
| 5,328,453 A * | 7/1994 | Sibalis | 604/20 |
| 5,358,483 A | 10/1994 | Sibalis | |
| 5,443,442 A * | 8/1995 | Phipps et al. | 604/20 |
| 5,458,569 A | 10/1995 | Kirk, III et al. | |
| 5,466,217 A | 11/1995 | Myers et al. | |
| 5,533,971 A | 7/1996 | Phipps | |
| 5,540,669 A * | 7/1996 | Sage et al. | 604/290 |
| 5,582,587 A | 12/1996 | Gyory et al. | |
| 5,605,536 A * | 2/1997 | Sibalis | 604/20 |
| 5,651,768 A | 7/1997 | Sibalis | |
| 5,685,837 A | 11/1997 | Horstmann | |

(Continued)

FOREIGN PATENT DOCUMENTS

| | | |
|---|---|---|
| WO | WO 00/12172 | 3/2000 |
| WO | WO 01/49365 | 7/2001 |

*Primary Examiner* — Manuel Mendez
*Assistant Examiner* — Ian Holloway
(74) *Attorney, Agent, or Firm* — Bret E. Field; Daniel G. Stoddard; Bozicevic, Field & Francis, LLP

(57) ABSTRACT

A disposable skin-worn device for the transdermal delivery at least one dose of charged therapeutic substances, including granisetron, by iontophoresis, the device comprising a donor reservoir containing an amount of a therapeutic substance to be delivered transdermally by iontophoresis, a counter reservoir, a source of electric power connected in a circuit between the donor reservoir and the counter reservoir and a control system for controlling current flow in the circuit to enable at least one dose of the therapeutic substance to be delivered transdermally by iontophoresis and wherein the control system includes a control element selected from the group consisting of a sensor activated by an external signal and a switch.

26 Claims, 1 Drawing Sheet

U.S. PATENT DOCUMENTS

| | | | | |
|---|---|---|---|---|
| 5,697,896 | A * | 12/1997 | McNichols et al. | 604/20 |
| 5,738,647 | A * | 4/1998 | Bernhard et al. | 604/20 |
| 5,954,684 | A * | 9/1999 | Flower et al. | 604/20 |
| 5,993,435 | A * | 11/1999 | Haak et al. | 604/501 |
| 6,004,309 | A * | 12/1999 | Phipps | 604/501 |
| 6,047,208 | A | 4/2000 | Flower | |
| 6,059,736 | A | 5/2000 | Tapper | |
| 6,086,572 | A * | 7/2000 | Johnson et al. | 604/503 |
| 6,169,920 | B1 | 1/2001 | Haak et al. | |
| 6,171,294 | B1 | 1/2001 | Southam et al. | |
| 6,216,033 | B1 | 4/2001 | Southam et al. | |
| 6,238,381 | B1 | 5/2001 | Tapper | |
| 6,317,629 | B1 | 11/2001 | Haak et al. | |
| 6,421,561 | B1 | 7/2002 | Morris | |
| 6,425,892 | B2 | 7/2002 | Southam et al. | |
| 6,477,410 | B1 | 11/2002 | Henley et al. | |
| 6,485,437 | B1 | 11/2002 | Tapper | |
| 6,597,946 | B2 | 7/2003 | Avrahami et al. | |
| 6,611,706 | B2 | 8/2003 | Avrahami et al. | |
| 6,653,014 | B2 | 11/2003 | Anderson et al. | |
| 6,678,554 | B1 | 1/2004 | Sun et al. | |
| 6,711,435 | B2 | 3/2004 | Avrahami | |
| 6,745,071 | B1 | 6/2004 | Anderson et al. | |
| 6,758,099 | B2 | 7/2004 | Cima et al. | |
| 6,801,804 | B2 * | 10/2004 | Miller et al. | 604/20 |
| 6,862,473 | B2 * | 3/2005 | Keusch et al. | 604/20 |
| 6,949,081 | B1 | 9/2005 | Chance | |
| 7,047,069 | B2 * | 5/2006 | Joshi | 604/20 |
| 2002/0188241 | A1 * | 12/2002 | Morris et al. | 604/20 |

* cited by examiner

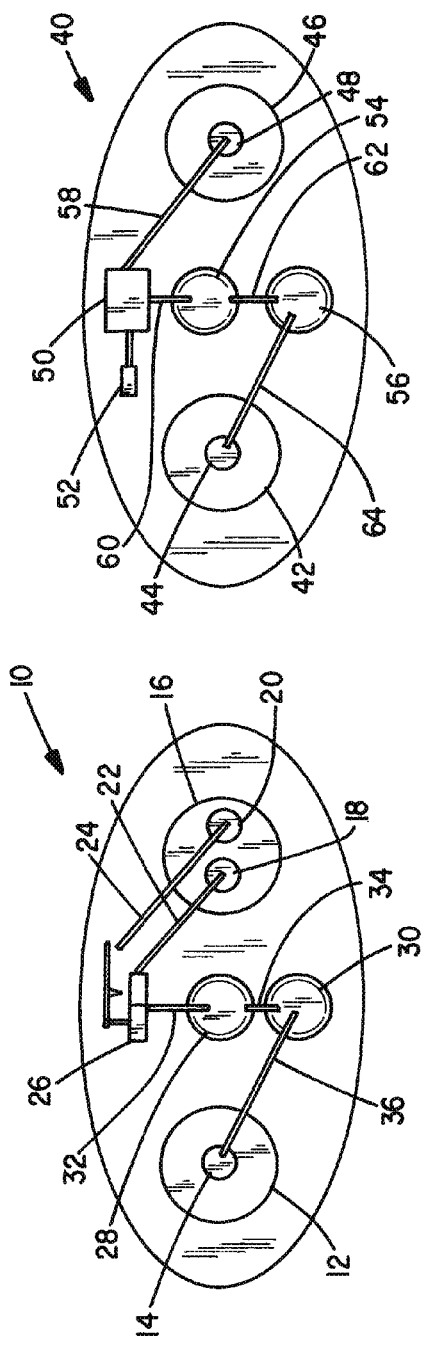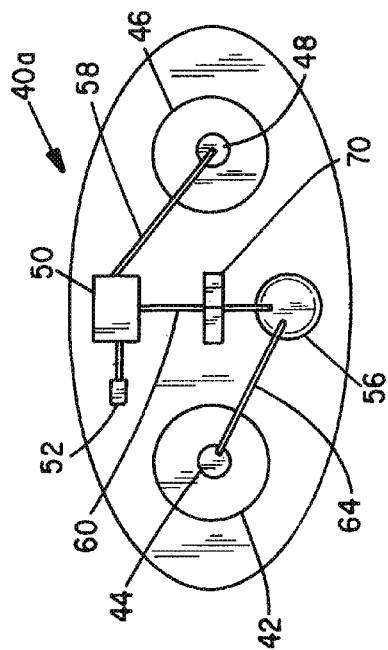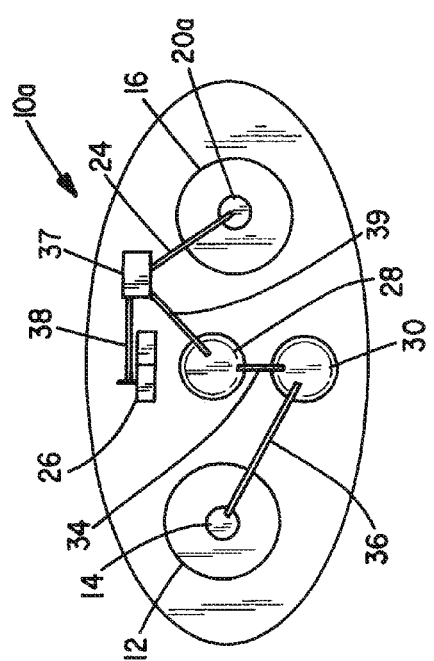

TRANSDERMAL SYSTEMS FOR THE DELIVERY OF THERAPEUTIC AGENTS INCLUDING GRANISETRON USING IONTOPHORESIS

CROSS-REFERENCED TO RELATED APPLICATIONS

This application is a continuing application of application Ser. No. 11/112,196, filed Apr. 22, 2005, and claims priority from that application, which is also deemed incorporated by reference in its entirety in this application.

STATEMENT REGARDING FEDERALLY SPONSORED RESEARCH OR DEVELOPMENT

Not applicable

BACKGROUND OF THE INVENTION

I. Field of the Invention

The present invention is related generally to transdermal delivery of therapeutic agents by the use of an applied electromotive force (emf), commonly known as iontophoresis. More specifically, this invention relates to the transdermal delivery of agents such as the anti-emesis agent granisetron.

II. Related Art

The process of iontophoresis was described by LeDuc in 1908 and has since found commercial use in the delivery of ionically charged therapeutic agent molecules such as pilocarpine, lidocaine and dexamethasone. In this delivery method, ions bearing a positive charge are driven across the skin at the site of an electrolytic electrical system anode while ions bearing a negative charge are driven across the skin at the site of an electrolytic system cathode.

Earlier, and some present, iontophoretic devices have been typically constructed of two electrodes attached by adhesive materials to a patient, each connected by a wire to a remote power supply, generally a microprocessor-controlled electrical instrument. More recently, self-contained wearable iontophoretic systems have been developed. These systems are advantageous in that they do not have external wires and are much smaller in size. Examples of such systems can be found in a variety of U.S. patents, examples of which include U.S. Pat. Nos. 4,927,408; 5,358,483; 5,458,569; 5,466,217; 5,533,971; 5,605,536; 5,651,768; 5,685,837; 6,421,561; WO 00/12172; U.S. Pat. No. 6,653,014. These systems also include two electrodes fixed to the skin of patients by means of adhesive materials.

Unlike passive delivery patches, iontophoretic devices can incorporate an ability to modify delivery rates with simple adjustments to the magnitude of current flow. This ability can be used to create a wearable system, wherein patients can self-adjust medication delivery in accordance to individual needs. U.S. Pat. Nos. 6,171,294; 6,216,033; 6,425,892; and 6,745,071 describe iontophoretic devices where patients can self-adjust pain management dosing of fentanyl or sufentanyl using either on-demand bolus dosing or changes in continuous delivery rate.

Two-stage iontophoretic devices have also been described, where an initially high level of current can be used to induce a rapid onset of action, followed by a automated decrease in current to a lower continuous level in order to provide a "maintenance" dosage over an extended time-period. U.S Pat. Nos. 5,207,752 and 6,421,561 are examples that serve to describe devices having such staged delivery profiles.

The present invention relates to an improved application of iontophoresis useful for the treatment of emesis. Emesis, in the form of nausea and vomiting, commonly occurs following chemotherapy, post-operatively following treatment with anesthetic agents, or after exposure to biologic agents and/or radiation, possibly in a military setting. It will be appreciated that oral dosage forms are convenient, but are unreliable because in the case of emesis, patients may be unable to keep the medication ingested. Granisetron is a selective antagonist of 5-hydroxytryptamine (5-HT3) receptors, and commercially available in oral or injectable dosage forms. It is known to be an effective agent for the management of emesis, as both a primary dose and as a "rescue dose" medication. The term "rescue dose" is defined as an additional dose necessary to treat breakthrough or recurring symptoms. For additional information see, for example, "Dose finding study of granisetron in patients receiving high-dose cisplatin chemotherapy", by A. Riviere in Br. J. Cancer, 69, 967-971 (1994), which provides an informative summary of clinical effectiveness of granisetron administered both as primary and rescue dosing medication.

As to the mode of administration, the disadvantage of oral administration is evident as noted above. A disadvantage of injectable administration forms lies in the invasive nature of injections, which can be painful, require clinical skill, can lead to infection, and are therefore are not suitable to self administration in a field or home setting.

Recognizing the shortcomings of oral and injectable dosage forms for granisetron, several companies have described methodologies for a transdermal administration process. Included are delivery systems for transdermal administration by: passive patches, heated passive patches, passive patches applied onto RF treated skin, and spray-on-skin systems where the total amount applied is fixed and delivery is improved by co-formulated permeation enhancers.

One advantage of transdermal systems is an ability to provide a sustained release of medication over time, which may serve to provide a longer duration of action. However, a significant limitation and disadvantage of passive transdermal administration is a slow onset of sufficient action to provide relief. It is not uncommon for a passive transdermal patch to take several hours (3 or more) before a therapeutic dosage is achieved. With passive transdermal delivery, the skin can act as a depot, and release to the bloodstream will not occur until that skin depot area is saturated. This slow onset of action acts as a clinical limitation in two respects: 1) it cannot replace an existing oral or injectable form because it is a necessity to apply a patch several hours prior to a chemotherapy or operative procedure, and 2) a slow acting transdermal patch cannot reasonably serve as a rescue medication form, where a patient will prefer, for obvious reasons, a faster acting treatment. This second limitation is significant, in that it has been shown that, in many cases of highly emetogenic therapies, such as high dose chemotherapy, a significant percentage of patients will not be adequately served by a first, primary dosage form alone.

A more rapid onset of action can be achieved transdermally by using a system that includes iontophoresis. Granisetron in its hydrochloride salt form, is positively charged and can be delivered rapidly from a positively charged anode pad. Recent reports, for example, Scientific Abstract 1: Evaluation of iontophoretic permeation kinetics of granisetron through skin by subcutaneous microdialysis, presented at the 2003 AAPS meeting October, 2003; Scientific Abstract 2: IVIVC of Iontophoretic Delivery of granisetron by subcutaneous microdialysis, presented at the 2004 AAPS meeting October, 2004, have demonstrated that with iontophoresis, a therapeutic dosage can be achieved (in a hairless rat animal model) within approximately two-hours.

The two-hour system described in the reports, however, is not likely to provide additional benefit for emesis which may occur for up to several days after an exposure to an emetogenic procedure. Additionally, even the two-hour timeframe for achievement of a therapeutic dosage level is also an unacceptably long period of time necessary for clinician and patient to be waiting prior to an emetogenic treatment such as chemotherapy. Finally, the known iontophoresis patches do not provide a means to administer a second or rescue dosage for emesis management in the event the primary dosing from the patch is inadequate.

Therefore, a need exists for a simple-to-operate, inexpensive transdermal dosage form which can not only provide benefit afforded by a transdermal release of agents such as granisetron, but can also provide an initial or primary dose and one or more follow-on self-administered rescue doses treatment very rapidly.

SUMMARY OF THE INVENTION

The present invention provides a transdermal iontophoresis device and method that has the ability to administer a bolus dosage of a therapeutic agent, particularly a therapeutic granisetron bolus dosage rapidly using a single-use, disposable transdermal patch. In the case of granisetron, the patch of the invention provides an onset of a therapeutic level of action in generally less than one hour. Additionally, at least one embodiment of the patch device enables a patient to rapidly self-administer at least a second or rescue dose after the initial primary dose.

In one embodiment illustrating the invention, there is provided a disposable skin-worn patch device for the transdermal delivery of a plurality of doses of a charged therapeutic substance such as granisetron by iontophoresis. The device includes a reservoir from which the therapeutic agent is delivered into the body (donor reservoir) containing an amount of the substance to be delivered transdermally by iontophoresis and one or more donor electrodes, a counter reservoir containing a counter electrode which serves to complete the electrical circuit through the body, a source of electric power connected in a circuit between the donor reservoir and the counter reservoir and a user-operable control system for controlling current flow in the circuit to enable a plurality of successive doses of therapeutic substance to be administered from the donor reservoir. The multiple doses may be controlled by switching and selectively connecting each one of a plurality of donor electrodes designed to be oxidized or reduced in the iontophoresis circuit operation.

Those skilled in the art will recognize that microprocessor or other electronic or electrical control circuits can be used to regulate the rate of current flow, and therefore the rate of medication delivery. In an alternative embodiment, such a control circuit is implemented to create a device which can provide bolus and/or alternative waveform dosing from a single donor electrode configuration.

A first dose may be provided automatically by the application of the patch to the skin of a patient by a predetermined switching device in the circuit. Optionally, the patch also can be employed to supply a sustained, lower-level delivery rate of granisetron following an initial bolus dose. Such as system is illustrated and described, for example, in U.S. Pat. No. 6,421,051 assigned to the same assignee as the present application and which is deemed incorporated herein by reference for any purpose.

In another detailed embodiment, a disposable skin-worn patch is provided that incorporates an activation system to automatically administer granisetron after a sensor triggers the system based on an alarm signal. That control system is designed to respond to an externally generated signal, such as a radio frequency signal which may be given to a plurality of such devices as might be worn by soldiers in a military setting. A switch device may be provided in the circuit to prevent accidental activation from occurring in stored patches.

Whereas other substances may be delivered from either an anode or a cathode chamber, using the iontophoresis device of the invention, as indicated above, one preferred therapeutic substance to be delivered is granisetron. The granisetron may preferably be contained in a hydrogel formulation and preferably as a charged species which can only successfully be delivered in a therapeutic dose utilizing an active iontophoresis technique. Generally, granisetron and other therapeutically active species contained in an ionic or charged form, for iontophoresis deliveries migrate transdermally only slightly using passive application systems. Such an approach would not deliver a therapeutically effective level of material. Hydrogels based on polyvinylalcohol, hydroxypropylmethylcellulose (HPMC), and polyethylene oxide are examples of hydrogels that can co-formulated with the granisetron.

A therapeutic dose of granisetron is generally accepted to be between about 300 µg and 1000 µg. Patches in accordance with the present invention have the capacity to administer or deliver a bolus dosage between about 300 µg and 1000 µg, in less than about 1 hour. In this regard, it has been determined that an iontophoretic charge dosage between 20 and 60 mAmin can be used to successfully deliver this amount, so that current in the range of 0.3 and 1.0 mA would be required for a one-hour delivery period. Further, it has been learned that an optimal range of current density falls between 50 µA and 250 µA per square centimeter. Therefore, the delivery pad contact area needs to be sized with consideration given to this as a desired current density range.

With respect to the successful and rapid administration of granisetron by iontophoresis, it has also been determined that the total granisetron content supplied in the donor reservoir or pad should exceed the desired total quantity to be delivered by a significant amount. Generally, this has been found to be a factor of two or even more. Thus, if the desired total dosage to be delivered, for example, is 2 milligrams (2 mg), it has been found that at least 4 mg should be provided in the donor reservoir or pad. Generally, significant loss of delivery efficiency is seen in a second or rescue dose if the total content of granisetron in the patch is less than twice the total amount of granisetron desired to be delivered.

BRIEF DESCRIPTION OF THE DRAWINGS

In the drawings where like reference characters depict like parts:

FIG. 1 is a schematic representation of an embodiment of a transdermal patch in accordance with the invention capable of delivering a plurality of doses of a therapeutic agent;

FIG. 2 is a schematic representation of an alternate embodiment of a transdermal patch in accordance with the invention selectively designed to be activated by an external signal;

FIG. 3 is a schematic representation of another embodiment of the invention capable of delivering a plurality of doses of a therapeutic agent utilizing a single donor electrode; and FIG. 4 is a schematic representation of an embodiment similar to that in FIG. 2 including an element to preclude untimely activation.

DETAILED DESCRIPTION

The detailed description contained in this specification is intended to illustrate the principles of the invention and not to limit them. A limited number of illustrative embodiments are presented as examples and, it is anticipated, that others would occur to those skilled in the art which would be within the scope of the inventive concept.

FIG. 1 represents an iontophoretic patch device that automatically releases a dosage of granisetron or other therapeutic agent upon application of the device to the skin. That device is additionally capable of releasing a second dosage after a patient activates a switching device.

The embodiment of FIG. 1 illustrates an iontophoretic self-powered skin-applied adhesive patch device generally at 10. The patch includes a cathode chamber or counter reservoir 12 containing a cathode or counter electrode 14 and an anode chamber or donor reservoir 16 containing a pair of anodes 18 and 20 spaced and electrically isolated from each other, but electrically connected to respective conductors 22 and 24 and to the material in the reservoir 16. A two-position switch element is shown at 26 and a pair of power sources, which may be conventional button-type batteries are shown connected in series at 28 and 30. Additional interconnecting conductor elements are shown at 32, 34 and 36. Thus, using the switch 26, either anode 18 or 20 can be selectively connected or patched into a circuit which is completed by the application of the patch 10 to the skin of a patient, as is well known.

The charge capacity and so the dosage associated with either anode 18 or 20 can further be adjusted to any desired amount as by adjusting the content of oxidizable species at each anode such that depletion of the oxidizable species or isolation of the connection will produce an open circuit condition with that anode connected. Techniques for this are illustrated and described in U.S. Pat. No. 6,653,014 assigned to the same assignee as the present application and which is hereby incorporated by reference herein for any purpose.

Although one and two-anode devices are shown in the figures, it will be appreciated that, optionally, additional anodes, conductors and switch positions could readily be added, if desired. The circuit, optionally, can include elements to limit or control current flow in a known manner to produce a longer-lasting lower dosage at any switch position. For example, it may be desired to administer a low steady dose of granisetron of perhaps about 40 μg/hr over a long period of time after an initial bolus or first primary dose has been administered. Also, additional or other types of DC power sources and controls including programmed controls optionally such as shown in FIG. 3, for example, can be used. In operation, when the iontophoresis patch device of FIG. 1 is adhesively applied to the skin of a patient, this will complete a first circuit including a selectively included anode 18, 20 and the patch will immediately activate and begin to deliver a dosage of granisetron or other therapeutic agent contained in the anode or donor reservoir commensurate with the amount of oxidizable species available to the circuit at the then connected anode. This will preferably be preset by the position of the switch 26 set at the point of manufacture so that a known initial bolus of the granisetron as an initial therapeutic dosage can be delivered rapidly as soon as the device is applied to the skin of a user. Thereafter, if a second or so-called "rescue" dose is required, it can be triggered when the user operates the switch 26 to the alternate position to connect a second or alternate anode 18, 20 in the circuit to self-administer an additional dose of granisetron.

The alternate embodiment of FIG. 2 includes a similar skin-applied, self-powered adhesive patch 40 which includes a cathode chamber or counter reservoir 42 with cathode or counter electrode 44, an anode chamber or donor reservoir 46 provided with a single anode or donor electrode 48. A normally open switch or other activation element or device 50, connected with an associated sensor 52 for receiving external activation signals, is provided in the circuit between anode 48 and a pair of series-connected power sources 54 and 56. Connecting conductive elements are shown at 58, 60, 62 and 64.

This embodiment is designed to be worn by one potentially in need of receiving a dose of the therapeutic material of the patch. Activation of the patch and delivery of the medication, however, is controlled by an externally generated signal being received by sensor 52 which, in turn, triggers the element 50 to close a switch or otherwise function to complete the circuit. The embodiment 40 is shown with a single anode and so is designed to deliver a single dose to the wearer.

It will be appreciated that the sensing device 52 may be designed to receive any of many types of signals including radio frequency, audio, infrared, etc., and a single signal may activate the patches of many wearers as might occur among troops commonly engaged in a military setting. This embodiment provides a means for automated iontophoretic transdermal granisetron administration in a military field setting, as may be required for example, with an unexpected exposure of soldiers to radiation and/or chemical and biological agents.

FIG. 4 depicts a sensor-activated embodiment 40a, similar to that shown in FIG. 2 that is provided with a user activated element to provide protection against unwanted activation of the patch (such as in storage). Thus, the embodiment of FIG. 4 is provided with a manually-operated switch as at 70 which is designed to be closed by the user prior to sensor-controlled activation. In an open position, switch 70 interrupts the power on conductor 60 thereby disconnecting the power source 56. The closing of the switch 70 also actives the sensor 52 which is otherwise in an off mode. This embodiment is shown with a single power source 56 but as was the case in the embodiment of FIG. 2, additional power sources, or other controls as in FIG. 3, of course, may be used. Once the switch 70 is adjusted to the closed position by the user, the system is enabled for automated sensor-controlled activation.

A further embodiment 10a is shown in FIG. 3 in which an electronic control circuit or element 37 is connected by a conductor 38 to switch 26 and by a conductor 39 to power source 28. The electronic control circuit element 37 may include a microprocessor or a microprocessor-operated control which may be a timing controller such as are well known and which may operate in conjunction with a single donor electrode 20a to deliver a plurality of doses from the patch as controlled by the element 37 and switch 26. This is an alternative operating scheme to that of sequential electrode depletion shown in FIG. 1. The control system may be used to provide a sustained or steady low-level delivery of therapeutic agent. In the case of granisetron, this may be about 30-50 μg/hr and preferably about 40 μg/hr, for example.

The examples of the detailed description show the administration of a therapeutic agent in which the donor reservoir is the anode chamber. Of course, as previously indicated, for example, it will be recognized by those skilled in the art that an oppositely charged material might be administered using the cathode chamber as the donor reservoir and the anode chamber as the counter reservoir. Other variations in configuration and control are also contemplated. These may include circuit components to control delivery power over time or the like.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, as well as materials, can be accomplished without departing from the scope of the invention itself.

What is claimed is:

1. A method of providing transdermal delivery of a plurality of doses of a charged therapeutic substance comprising:
    (a) providing a skin-worn device comprising:
        (1) a donor reservoir containing an amount of a therapeutic substance to be delivered transdermally by iontophoresis, said donor reservoir further including circuit elements configured to deliver a plurality of successive doses of a therapeutic substance by sequentially selectively connecting a plurality of separate sources of reactive material in said circuit in a manner such that each dose is delivered by a different source of reactive material;
        (2) a counter reservoir;
        (3) a source of electric power connected in a circuit between said donor reservoir and said counter reservoir; and
        (4) a control system for controlling current flow in said circuit and configured to enable the plurality of successive doses of said therapeutic substance to be administered from said donor reservoir;
    (b) applying said skin-worn device to the skin of a patient; and
    (c) using said control system to control current flow in said circuit to provide a plurality of doses of said therapeutic substance.

2. A method as in claim 1 wherein said separate sources of reactive material are donor electrodes and said control system further comprises a switch operable for selectively connecting said donor electrodes into said circuit.

3. A method as in claim 1 wherein a circuit is completed and a first dose of said therapeutic substance is provided automatically upon application of said device to a patient's skin.

4. A method as in claim 2 wherein said switch is a two-position switch used by said patient to administer a second dosage when desired.

5. A method as in claim 1 wherein said therapeutic substance includes an anti-emesis agent.

6. A method as in claim 4 wherein said therapeutic substance includes an anti-emesis agent.

7. A method as in claim 5 wherein said anti-emesis agent comprises granisetron.

8. A method as in claim 6 wherein said anti-emesis agent comprises granisetron.

9. A method as in claim 7 wherein each said dose is between about 300 µg and 1000 µg.

10. A method as in claim 8 wherein each said dose is between about 300 µg and 1000 µg.

11. A method as in claim 9 wherein at least the first dose is delivered in about 1 hour.

12. A method as in claim 10 wherein at least the first dose is delivered in about 1 hour.

13. A method as in claim 7 wherein said granisetron is contained in a hydrogel formulation.

14. A method as in claim 8 wherein said granisetron is contained in a hydrogel formulation.

15. A method as in claim 1 wherein said control system includes a control element comprising a sensor activated by an externally generated signal to initiate delivery of a dose of said therapeutic substance from a patch device previously applied to the body of a user.

16. A method of administering granisetron to the body of a patient comprising:
    (a) providing a disposable skin-worn patch device for the delivery of granisetron by iontophoresis, capable of providing a plurality of doses of granisetron to the body, comprising:
        (1) a donor reservoir containing granisetron, said donor reservoir further including circuit elements configured to deliver a plurality of successive doses of granisetron by sequentially selectively connecting a plurality of separate sources of reactive material in said circuit in a manner such that each dose is delivered by a different source of reactive material;
        (2) a counter reservoir;
        (3) a source of electrical power; and
        (4) a control system configured for controlling administration using a first completed circuit for supplying a primary dose of between about 300 µg and about 1000 µg of granisetron in a less than 2-hour time period upon application of the patch to the body surface, and user-operable device to allow user to self-administer sequentially an additional dose of between about 300 µg and about 1000 µg of granisetron;
    (b) applying said device to the skin of a patient; and
    (c) using said user operable device to administer an additional dose of granisetron when desired.

17. A method as in claim 16 wherein said granisetron is contained in a hydrogel formulation.

18. A method as in claim 5 wherein said granisetron is in a form that can only be delivered by iontophoresis.

19. A method as in claim 7 wherein said control system provides steady low level delivery of about 40 µg/hr of granisetron after said first primary dose.

20. A method as in claim 1 wherein said donor reservoir contains a single source of reactive material.

21. A method as in claim 20 wherein said control circuit electronically controls dosage administration.

22. A method as in claim 1 wherein the amount of therapeutic substance supplied in the donor reservoir exceeds a desired total quantity to be delivered by the device to a user.

23. A disposable skin-worn device for the transdermal delivery of a plurality of doses of a charged therapeutic substance by iontophoresis comprising:
    (a) a donor reservoir containing an amount of a therapeutic substance to be delivered transdermally by iontophoresis, said donor reservoir further including elements configured to deliver a plurality of successive doses of a therapeutic substance by sequentially selectively connecting a plurality of separate sources of reactive material in said circuit in a manner such that each dose is delivered by a different source of reactive material;
    (b) a counter reservoir;
    (c) a source of electric power connected in a circuit between said donor reservoir and said counter reservoir; and
    (d) a user-operable control system configured to enable the plurality of successive doses of said therapeutic substance to be administered from said donor reservoir.

24. A method as in claim 2, wherein the content of reactive material at each donor electrode is such that depletion of the reactive material produces an open circuit condition with that electrode connected.

25. A method of providing transdermal delivery of a plurality of doses of a charged therapeutic substance to a patient, the method comprising:
 (a) applying to a skin site of the patient a skin-worn device comprising:
  (i) a donor reservoir containing an amount of a therapeutic substance to be delivered transdermally by iontophoresis, said donor reservoir further including circuit elements configured to deliver a plurality of successive doses of a therapeutic substance by sequentially selectively connecting a first and second electrode in a manner such that each dose is delivered by a different electrode;
  (2) a counter reservoir;
  (3) a source of electric power connected in a circuit between said donor reservoir and said counter reservoir; and
  (4) a control system for controlling current flow in said circuit and configured to enable the plurality of successive doses of said therapeutic substance to be administered from said donor reservoir;
 (b) controlling current flow in said circuit in a manner sufficient to iontophoretically deliver said therapeutic substance by said first electrode until said first electrode's reactive species is depleted; and
 (c) controlling current flow in said circuit in a manner sufficient to iontophoretically deliver said therapeutic substance by said second electrode.

26. The method as in claim 25, wherein the first and second electrodes are anodes and the reactive species is an oxidizable species.

* * * * *